United States Patent [19]

Diamond

[11] Patent Number: 4,663,351
[45] Date of Patent: May 5, 1987

[54] DOBUTAMINE TRI-ISOBUTYRIC ACID ESTER AND THE USE THEREOF AS A CARDIOTONIC AGENT

[75] Inventor: Julius Diamond, Mountain Lakes, N.J.

[73] Assignee: Berlex Laboratories, Inc., Cedar Knolls, N.J.

[21] Appl. No.: 768,779

[22] Filed: Aug. 23, 1985

[51] Int. Cl.$^4$ .................... A61K 31/22; C07C 101/00
[52] U.S. Cl. .................................... 514/548; 560/138
[58] Field of Search ......................... 560/138; 514/548

[56] References Cited

U.S. PATENT DOCUMENTS

| | | | |
|---|---|---|---|
| 2,276,619 | 3/1942 | Kulz | 564/381 |
| 3,987,200 | 10/1976 | Tuttle et al. | 514/654 |
| 4,340,603 | 7/1982 | Bodor et al. | 514/509 |
| 4,562,206 | 12/1985 | Tuttle | 514/548 |

FOREIGN PATENT DOCUMENTS 2146529 4/1985 United Kingdom .

*Primary Examiner*—Natalie Trousof
*Assistant Examiner*—Patricia M. Scott
*Attorney, Agent, or Firm*—Elizabeth A. Bellamy; John L. White; I. William Millen

[57] ABSTRACT

A novel, orally administrable pro-drug form of dobutamine of the formula

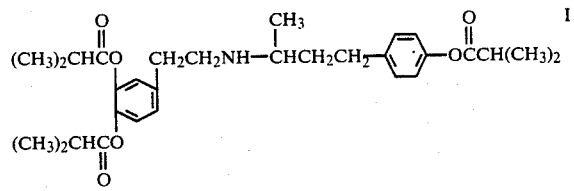

or a pharmaceutically acceptable acid addition salt thereof.

6 Claims, No Drawings

DOBUTAMINE TRI-ISOBUTYRIC ACID ESTER AND THE USE THEREOF AS A CARDIOTONIC AGENT

FIELD OF INVENTION

This invention relates to novel compositions of matter, to methods for their production, and to their use as cardiotonic agents in orally administrable pharmaceutical compositions. Specifically, this invention relates to a pro-drug form of a dobutamine, more specifically to 4-[2-[[3-(4-hydroxyphenyl)-1-methylpropyl]amino]ethyl]-1,2-benzenediol tri-isobutyric acid ester or a pharmaceutically acceptable acid addition salt thereof and its use as an orally administrable cardiotonic agent in the treatment of congestive heart failure.

BACKGROUND OF THE INVENTION

One of the few drugs available for use in the United States for the treatment of congestive heart failure, whereby such treatment is to provide positive inotropic support for the heart, is the compound dobutamine (Dobutrex® for injection; brand name E. Lilly). Dobutamine or 4-[2-[[3-(4-hydroxy-phenyl)-1-methylpropyl]amino]ethyl]-1,2-benzenediol, however, is not orally effective and so is used primarily as an injectable in a clinical setting. The object of this invention is to provide an orally active and administratable pro-drug of dobutamine, that is, its tri-isobutyric acid ester.

GENERAL DESCRIPTION OF THE INVENTION COMPOSITION OF MATTER ASPECT

This invention relates to the compound of the following Formula I:

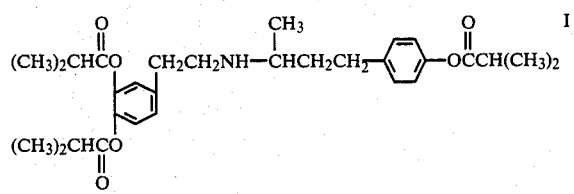

which is 4-[2-[[3-(4-hydroxyphenyl)-1-methylpropyl]amino]-ethyl]-1,2-benzenediol tri-isobutyric acid ester and to the pharmaceutically acceptable acid addition salts thereof. Such salts, prepared by methods well known in the art, are formed with both inorganic and organic acids, e.g. hydrochloric, hydrobromic, sulfuric, phosphoric, acetic, propionic, benzoic, naphthoic, oxalic, succinic, maleic, malic, adipic, lactic, tartaric, citric, salicyclic, methanesulfonic, and p-toluenesulfonic acids.

The compound of Formula I contains an asymmetric centre, therefore, one pair of optical isomers is possible. It is to be understood that the definition of the Formula I compound encompasses all possible stereoisomers and mixtures thereof, which possess the activity discussed herein. In particular, it encompasses both the racemic form and isolated optical isomers which possess the indicated activity. Most especially it encompasses the following compounds (±)-[2[[3-(4-hydroxyphenyl)-1-methylpropyl]amino]ethyl]-1,2-benzenediol tri-isobutyric acid ester; (+)-4-[2-[[3-(4-hydroxyphenyl)-1-methylpropyl]-amino]ethyl]-1,2-benzenediol tri-isobutyric acid ester and (−)4-[2-[[3-(4-hydroxyphenyl)-1-methylpropyl]-amino]ethyl]-1,2-benzenediol tri-isobutyric acid ester, otherwise named respectively (±)-dobutamine tri-isobutyric acid ester, (+)-dobutamine tri-isobutyric acid ester, (−)-dobutamine tri-isobutyric acid ester and their pharmaceutically acceptable acid addition salts. The individual optical isomers can be obtained from the racemate by standard procedures, such as by forming a salt with an optically active acid followed by fractional crystallization, and separation of the diastereoisomeric salts. Alternatively, the optical isomers can be obtained directly by reacting isobutyroyl chloride with the corresponding (+)dobutamine or (−)dobutamine.

PROCESS ASPECT OF THE INVENTION

A variety of procedures are available for the preparation of the compounds of this invention as would be apparent to those skilled in the art. The most convenient route makes use of the compound dobutamine, as a free base or as one of its acid salts of the hydrobromic or hydrochloric variety, which is reacted with isobutyrol chloride in the presence of trifluoroacetic acid. The preparation of dobutamine is illustrated in U.S. Pat. No. 3,987,200.

Further novel tri-esters of dobutamine prepared for comparative purposes in this invention are exemplified in the Examples section of this invention.

METHOD OF USE AND PHARMACEUTICAL COMPOSITION ASPECT

The number one killer in the United States is the disease state caused by various cardiovascular idiosyncrasies. Of these, a large portion can be classified as congestive heart failure (CHF).

The treatment of CHF is effected by various methods (1) enhancement of the contractile state of the myocardium with positive inotropic agents, (2) adjustment of the peripheral circulatory state with peripheral vasodilators, (3) reduction in volume with diuretics or (4) a combination of these therapeutic approaches.

In the United States there are two classes of drugs available for the treatment of CHF, whereby the principal mode of action is to provide positive inotropic support for the heart. This type of drug is known as a cardiotonic agent. The two classes are the cardiac glycosides (e.g., digitoxin and digoxin) and the sympathomimetic agents (e.g., dopamine and dobutamine). The cardiac glycosides are orally effective agents. Their use, however, is limited by their arrhythmogenic liability. Dobutamine and dopamine are limited by lack of oral effectiveness. Recently, the non-sympathomimetic cardiotonic agent, amrinone, has been approved for use in the United States; however, this product has been approved only for injectable use.

In a society increasingly conscious of hospital costs, out-patient mobility and work force usefulness, the absence of safe, orally effective inotropic agents for the treatment of congestive heart failure has stimulated research in this area.

The aforementioned dobutamine is a selective β-inotropic agonist (cardiotonic agent) useful in the treatment of acute heart failure. The compound is rapidly inactivated by first-pass hepatic metabolism and as a consequence is not active by oral administration. It is short acting following a single intravenous dose, and therefore must be administered by continuous intravenous infusion. Since dobutamine is a catecholamine type compound—containing a 3-hydroxyl group on the phenyl ring, its rapid inactivation is caused by the formation of the 3-methoxy metabolite via the enzyme catechol-O-methyl transferase. This metabolite is an inactive compound.

The object of this invention was to block this O-methyl transferase reaction by masking the 3-hydroxyl function with a labile group which could be enzymatically removed to produce continuous levels of dobutamine. Such a masking should produce a pro-drug form of dobutamine. A pro-drug denotes a derivative of a known compound with certain characteristics which, after having been absorbed in the gut or bloodstream of a mammal, cleaves in such a manner as to release the known drug.

In view of the foregoing, fully esterified derivatives of dobutamine were prepared and tested as pro-drugs. Surprisingly, only one of a number of the wholly esterified derivatives of dobutamine exhibited an orally administratable profile. That compound, dobutamine tri-isobutyric acid ester, the subject of this invention, was compared against other wholly esterfied dobutamines, e.g., dobutamine tri-acetic acid ester, dobutamine tri-pivalic acid ester, dobutamine tri-isovaleric acid ester dobutamine tri-benzoyl acid ester and dobutamine itself.

The compounds, dissolved in a water-ethanol mixture and suspended in gum tragacanth and dosed by gavage, were tested in the pentobarbital-anesthesized dog; measuring mean blood pressure, heart rate, LV dp/dt, aortic blood flow and total peripheral resistance in order to ascertain the cardiotonic profile. The comparative results follow in Table I with the note that a 50 mg/kg dose of dobutamine tri-isobutyric acid ester corresponds to a 29.4 mg/kg dose of free dobutamine in terms of equivalent molecular weight.

TABLE I

RO–⟨⟩–CH$_2$CH$_2$NHCH(CH$_3$)–CH$_2$CH$_2$–⟨⟩–OR
(with RO– also on the first ring)

| # | R | mg/kg Dose | Activity | Duration Act. (Hrs.) |
|---|---|---|---|---|
| Dobutamine (A) | H | 29.4 | inactive | — |
| (B) | —C(O)—CH(CH$_3$)$_2$ | 12.5 | active | 2+ |
| (C) | —C(O)—C(CH$_3$)$_3$ | 250 | inactive | — |
| (D) | —C(O)—CH$_3$ | 25 | inactive | — |
| (E) | —C(O)CH$_2$CH(CH$_3$)$_2$ | 20 | inactive | — |
| (F) | —C(O)—φ | 25 | tremors | — |

In view of the above, this invention that is, dobutamine-tri-isobutyric acid ester or a pharmaceutically acceptable salt thereof, provides an orally administrable method of eliciting a cardiotonic effect in a mammalian host having a disease condition in which therapeutic benefit is derived from elicitation of a cardiotonic effect. Said cardiotonic effect will be useful in the treatment of the disease condition congestive heart failure.

Since the cardiotonic agent of this invention can be administered orally it can be compounded in the form of tablets or capsules, suspensions, elixirs or the like. Although oral administration is the preferable mode of utilizing the invention, the compound may also be administered parenterally (via intravenous or intramuscular injection), sublingually, buccally, or rectally.

The pharmaceutical carriers useful in the preparation of the foregoing formulations will include, for example, such substances as water, oils, fats, waxes, polyesters, alcohols, polyols and the like. In general, the dosage administered of a compound of this invention, will be dependent on the age and weight of the mammalian host being treated. Although it is envisioned the invention will find its primary usefulness in a human clinical setting, the compounds would certainly be useful in veterinary medicine. Therefore, said host (preferably but not exclusively human) is to be treated for a disease state, particularly the disease state CHF, receptive to being treated with a cardiotonic agent.

The precise dose will be dependent on the stage and severity of the disease. For instance, for the treatment of CHF, it is contemplated that oral dosing will be approximately 5 to 30 mg/kg b.i.d. or t.i.d. corresponding to dosage forms of 250 to 1500 mg/dose.

The invention described hereinabove is illustrated hereinbelow in the Examples and Formulations, which is not to be construed as limiting the scope of this invention.

EXAMPLES

EXAMPLE I

4-[2-[[3-(4-Hydroxyphenyl)-1-methylpropyl]amino]ethyl]-1,2-benzenediol tri-isobutyric acid ester hydrochloride; [Dobutamine tri-isobutyric acid ester hydrochloride].

To a suspension of 25.3 gm (0.066 mole) of dobutamine hydrobromide in 140 ml of trifluoroacetic acid is added 43 gm (0.396 mole) of isobutyroyl chloride. After the addition and the simultaneous evolution of hydrochloride acid gas, the resultant mixture is stirred at room temperature for 1 hour. The reaction mixture is evaporated and the residue is taken up in chloroform, washed three times with saturated sodium bicarbonate solution, then with water. The organic layer is dried over MgSO$_4$, filtered and evaporated to yield a brown oil.

The oil is dissolved in anhydrous water and gaseous HCl is bubbled into the solution. The solution is chilled and the resultant solid is filtered and recrystallized from benzene/pet. ether (1:1) to yield the subject compound.

NMR (CDCl$_3$): δ=1.30(d)+1.40(d), (total of 21H), 1.9–2.5(m, 2), 2.5–3.5(m, 10), 6.8–7.3(m, 7), 9.7(bs, 1)ppm.

EXAMPLE II

4-[2-[[3-(4-Hydroxyphenyl)-1-methylpropyl]amino]ethyl]1,2-benzenediol tri-isobutyric acid ester hydrobromide [Dobutamine tri-isobutyric acid ester hydrobromide].

The subject compound is prepared as in Example I, except the oil is dissolved in ether and gaseous HBr is bubbled into the solution. The title compound is isolated as in Example I.

NMR (CDCl$_3$): δ=1.30(d)+12.0-1.6(m) (total 21H), 2.5-3.4(m, 12), 6.8-7.2(m, 7, arom.)ppm.

EXAMPLE III

Tri-esters of Dobutamine

In a manner similar to Example I utilizing dobutamine and the appropriate acid chloride and a viable salt the following compounds were prepared.

(C) Dobutamine+pivaloyl chloride+hydrogen chloride=Dobutamine tri-pivalic acid ester hydrochloride
NMR (CDCl$_3$): δ=1.35(s)+1.3-1.6(m) (total of 30H), 2.2-3.4(m, 9), 6.8-7.2(m, 7, arom.), 9.8(bs, 2)ppm.

(D) Dobutamine+acetyl chloride+hydrogen chloride=Dobutamine tri-acetic acid ester hydrochloride
NMR (CDCl$_3$): δ=1.45(d, 3), 2.30(s, 9), 2.1-3.4(m, 9), 6.8-7.3(m, 7, arom.), 9.65(bs, 1.4)ppm.

(E) Dobutamine+isovaleroyl chloride+DL-tartaric acid=Dobutamine tri-isovaleric acid ester DL-tartaric acid salt
NMR (CDCl$_3$): δ=1.05(d, 18), 1.35(brd, 3), 1.5-3.0(br, 14), 3.10(br s, 4), 4.35(s, 2, tartaric acid), 5.9-6.8(br, s, 5, exchangeable), 6.85-7.35(m, 7)ppm.

(F) Dobutamine+benzoylchloride+phosphoric acid=Dobutamine tri-benzoic acid ester phosphate
NMR (CDCl$_3$): δ=0.8-3.8(br, 12), 6.8-7.5(m, 16), 7.6-8.2(m, 6), 8.3-10.2(br, 4, exchangeable)ppm.

FORMULATIONS

For convenience sake in the following formulations the subject compound, dobutamine tri-isobutyric acid ester hydrochloride, will be designated as DTIBAE.HCl.

| Formulation I Capsule Granulation | |
|---|---|
| Item: | mg/capsule |
| (1) DTIBAE.HCl | 250.0 |
| (2) Lactose Hydrous N.F. | 100.0 |
| (3) Microcrystalline cellulose N.F. | 40.0 |
| (4) Silica gel N.F. | 8.0 |
| (5) Magnesium stearate N.F. | 2.0 |
| | 400 mg |

Procedure:
A. Blend items 1, 3, and 4 in a suitable mixer, i.e., Lodige, Patterson-Kelley, Day, etc.
B. Pass Blend (A) through an appropriate milling device, i.e., Fitzmill, to achieve content uniformity.
C. After milling, place blend (B) into a suitable mixer and add item 2. Blend until a uniform mass is obtained.
D. To blend (C), add item 5 and continue blending until adequately dispersed.
E. Fill the final blend into the desired hard gelatin capsules using suitable capsule filling equipment.

| Formulation II Conventional Wet Granulation | |
|---|---|
| Item: | (mg/tab) |
| (1) DTIBAE.HCl | 250.0 |
| (2) Lactose Hydrous N.F. | 247.0 |
| (3) Corn Starch N.F. | 60.0 |
| (4) Povidone U.S.P. | 40.0 |
| (5) Magnesium Stearate N.F. | 3.0 |
| (6) Purified Water U.S.P. | Q.S. |
| | 600 mg |

Procedure:
A. Blend items 1, 2, 3, and 4 in a suitable mixer until a uniform mass is obtained, i.e., Lodige, Patterson-Kelley, Day, etc.
B. Slowly add item 6 to blend (A) to achieve the desired consistency of granulation.
C. Spread the granulated mass on appropriate drying trays and dry in appropriate drying equipment.
D. Pass the dried granulation through an appropriate milling device, i.e., Fitzmill, to obtain the appropriate particle size of the granulation.
E. Blend the milled granulation with item 5 in the appropriate blending equipment.
F. Compress the final blend into tablets using an appropriate tablet press and tooling.

| Formulation III Direct Compression Granulation | |
|---|---|
| Item: | (mg/tab) |
| (1) DTIBAE.HCl | 250.0 |
| (2) Lactose Anhyd. D.T.G. N.F. | 247.0 |
| (3) Microcrystalline Cellulose N.F. | 80.0 |
| (4) Corn Starch progelatinized N.F. | 20.0 |
| (5) Magnesium stearate N.F. | 3.0 |
| | 600 mg |

Procedure:
A. Blend items 1, 3, and 4 in a suitable mixer, i.e., Lodige, Patterson-Kelley, Day, etc.
B. Pass blend (A) through an appropriate milling device, i.e., Fitzmill, to achieve content uniformity.
C. After milling, place blend (A) into a suitable mixer and add item 2. Blend until a uniform mass is obtained.
D. To blend (C), add item 5 and continue blending until adequately dispersed.
E. Compress the final blend into tablets using an appropriate tablet press and tooling.

I claim:

1. A compound of the Formula I:

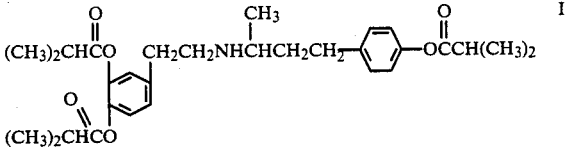

or a pharmaceutically acceptable acid addition salt thereof.

2. A compound of claim 1 which is 4-[2-[[3-(4-hydroxyphenyl)-1-methylpropyl]amino]ethyl]-1,2-benzenediol tri-isobutyric acid ester.

3. A compound of claim 1 which is 4-[2-[[3-(4-hydroxyphenyl)-1-methylpropyl]amino]ethyl]-1,2-benzendiol tri-isobutyric acid ester hydrochloride.

4. A compound of claim 1 which is 4-[2-[[3-(4-hydroxyphenyl)-1-methylpropyl]amino]ethyl]-1,2-benzenediol tri-isobutyric acid ester hydrobromide.

5. An orally administrable pharmaceutical composition which produces a cardiotonic effect comprising a non-toxic cardiotonically effective amount of a compound of claim 1 in admixture with a non-toxic pharmaceutically acceptable carrier.

6. An orally administrable method of eliciting a cardiotonic effect in mammalian host having a cardiovascular disease state in which therapeutic benefit is derived from elicitation of a cardiotonic effect, which comprises administering to said host a non-toxic cardiotonically effective amount of a compound of claim 1.

* * * * *

UNITED STATES PATENT AND TRADEMARK OFFICE
CERTIFICATE OF CORRECTION

PATENT NO. : 4,663,351

DATED : May 5, 1987

INVENTOR(S) : Julius Diamond

It is certified that error appears in the above-identified patent and that said Letters Patent is hereby corrected as shown below:

Column 1, line 29 "prodrug of dobutamine" should read
----pro-drug form of dobutamine----.

Column 4, line 52 "in anhydrous water" should read
----in anhydrous ether----.

Column 6, line 68 "-1,2-benzendiol" should read
---- -1,2-benzenediol----.

Signed and Sealed this

Ninth Day of February, 1988

Attest:

DONALD J. QUIGG

Attesting Officer

Commissioner of Patents and Trademarks